(12) United States Patent
Xiao et al.

(10) Patent No.: US 8,178,353 B2
(45) Date of Patent: May 15, 2012

(54) METHOD FOR DETERMINATION OF POLYMER CONCENTRATION IN WATER SYSTEMS

(75) Inventors: Caibin Xiao, Harleysville, PA (US); Yangang Liang, ShangHai (CN); Li Zhang, ShangHai (CN)

(73) Assignee: General Electric Company, Schenectady, NY (US)

( * ) Notice: Subject to any disclaimer, the term of this patent is extended or adjusted under 35 U.S.C. 154(b) by 608 days.

(21) Appl. No.: 11/755,935

(22) Filed: May 31, 2007

(65) Prior Publication Data
US 2008/0299665 A1 Dec. 4, 2008

(51) Int. Cl.
*C10B 57/00* (2006.01)
*C10N 70/00* (2006.01)

(52) U.S. Cl. ........ 436/85; 436/164; 422/400; 435/287.7
(58) Field of Classification Search .................... 436/85, 436/164; 422/400; 435/287.7
See application file for complete search history.

(56) References Cited

U.S. PATENT DOCUMENTS

| | | | |
|---|---|---|---|
| 2,591,904 A * | 4/1952 | Zola ........................ | 106/163.01 |
| 4,894,346 A | 1/1990 | Myers et al. | |
| 5,032,526 A | 7/1991 | Myers et al. | |
| 5,248,438 A | 9/1993 | Perez | |
| 5,271,862 A | 12/1993 | Freese | |
| 5,378,372 A | 1/1995 | Carey et al. | |
| 5,378,390 A | 1/1995 | Perez et al. | |
| 5,389,548 A | 2/1995 | Hoots et al. | |
| 5,489,666 A | 2/1996 | Carey et al. | |
| 5,518,629 A | 5/1996 | Perez et al. | |
| 5,575,920 A | 11/1996 | Freese et al. | |
| 6,214,627 B1 * | 4/2001 | Ciota et al. ..................... | 436/166 |
| 2003/0049857 A1 * | 3/2003 | Chan ............................. | 436/170 |

FOREIGN PATENT DOCUMENTS

| | | |
|---|---|---|
| EP | 0144130 A | 6/1985 |
| WO | WO 0058725 A | 10/2000 |
| WO | WO 0136542 A | 5/2001 |

OTHER PUBLICATIONS

International Search Report issued in connection with corresponding PCT Application No. US2008/061832 by the European Patent Office.

* cited by examiner

*Primary Examiner* — Krishnan S Menon
*Assistant Examiner* — Rebecca M Fritchman
(74) *Attorney, Agent, or Firm* — GE Global Patent Operation; Peter T. DiMauro (57) ABSTRACT

In one aspect, the invention is directed to a method for determining the concentration of anionic polymers or oligomers in industrial water comprising combining a buffer solution and a cationic dye solution, measuring absorbance of the buffer-dye admixture at selected wavelength(s) and determining the polymer or oligomer concentration from the previously determined absorbance values. In alternate embodiments of the invention, the buffer solution may be a multifunctional buffer solution and may be comprised of multiple buffers, masking agents. and/or stabilizing agents and combinations thereof. Other embodiments provide that multiple dyes may be employed.

22 Claims, 8 Drawing Sheets

METHOD FOR DETERMINATION OF POLYMER CONCENTRATION IN WATER SYSTEMS

BACKGROUND OF THE INVENTION

1. Field of the invention

The field of the invention relates generally to the detection of water-soluble polymers in industrial water systems, such as cooling and boiler water systems. More particularly, it relates to a method of determining the concentration or availability of anionic water-soluble polymers in industrial water systems based on the interaction between cationic dyes and water-soluble polymers.

2. Description of Related Art

It is well known to use water in numerous and varied industrial processes, such as removing heat from process equipment and the generation of steam. However, in most industrial processes it is not prudent or possible to use untreated water as the presence of impurities may impact the process in question. For example, compounds that inhibit scale formation are added to cooling tower and boiling water to prevent the formation or disposition of scale on the equipment used in these processes.

Most industrial waters contain metal cations such as calcium, barium, magnesium and sodium, as well as anions such as bicarbonate, carbonate, sulfate, phosphate and fluoride. When combinations of the cations and anions are present above certain concentrations, reaction products precipitate on the surface of the equipment in contact with the water in the process and form scale or deposits. The presence of such scale or deposits results in non-optimum process conditions and results in the cleaning or removal of such scale or deposits that is expensive and burdensome in that it often requires a shutdown of the process or system. Accordingly, in order to prevent such scale or deposits from occurring, it is preferable to treat the water with the proper chemicals in order to prohibit their formation.

Formation of scale and deposits can be avoided by insuring that the solubility of cation-anion reaction products is not exceeded. Certain chemicals are known to be useful for this purpose, including water-soluble polymers, such as polymers derived from unsaturated carboxlyates and unsaturated sulfonates and their salts. Some particularly useful water-soluble polymers include HPS-I, AEC and APES and polyepoxysuccinic acid (all available from GE Beta, Trevose, Pa.), and as further described in U.S. Pat. Nos. 5,518,629; 5,378,390; 5,575,920; 6,099,755; 5,489,666; 5,248,483; 5,378,372; and 5,271,862. However, the presence of these polymers causes additional issues of concern, as the concentration of the polymers in the industrial water systems must be carefully monitored. If too little polymer is employed, scaling may still occur, while if too much polymer is used, the treatment may not be cost effective. For each given system, there is an optimal concentration level or range that needs to be realized.

Methods are known for determining the concentration of water-soluble polymers in aqueous systems. For example, there are a number of methods available which determine the level of specific components using dyes. U.S. Pat. No. 4,894, 346 teaches a method for the calorimetric determination of polycarboxylates in aqueous systems with certain cationic dyes. U.S. Pat. No. 6, 214,627 to Ciota et al. measures the concentration of an anionically charged polymer in an aqueous solution that comprises a reagent, water, Nile Blue Dye and a chelant. In addition there is a Hach polyacrylic acid method that uses iron thiocyanate chelation to detect calibration based on polyacrylic acid. Other methods include the use of luminal-tagged polymers in combination with fluorescent or chemiluminescent detection techniques to monitor the industrial waters, such as in U.S. Pat. No. 5,958,778. As demonstrated in U.S. Pat. No. 6,524,350 many cationic dyes, are not stable in a solution state. In that patent, it is shown that that pinacyanol chloride is not stable in aqueous solutions. However, these methods have numerous shortcomings, including instability in aqueous systems, narrow dynamic range, and interference by naturally occurring polymers and sample ionic strength.

The current processes have many problems associated with them, particularly interference from various factors and components. Accordingly, a need exists for simplified and more accurate test methods that can easily be used to determine the concentration of water-soluble polymers in aqueous solutions, that exhibit high reproducibility, decreased response to interferences and enhanced stability.

SUMMARY OF THE INVENTION

In one aspect, the present invention is directed to a method for determining the concentration of anionic polymers or oligomers in industrial water comprising combining a buffer solution and a cationic dye solution, measuring absorbance of the buffer-dye admixture at selected wavelength(s) and determining the polymer or oligomer concentration from the previously determined absorbance values.

In alternate embodiments of the invention, the buffer solution may be a multifunctional buffer solution and may be comprised of multiple buffers, masking agents, and/or stabilizing agents and combinations thereof. Other embodiments provide that multiple dyes may be employed.

The various features of novelty that characterize the invention are pointed out with particularity in the claims annexed to and forming a part of this disclosure. For a better understanding of the invention, its operating advantages and benefits obtained by its uses, reference is made to the accompanying drawings and descriptive matter. The accompanying drawings are intended to show examples of the many forms of the invention. The drawings are not intended as showing the limits of all of the ways the invention can be made and used. Changes to and substitutions of the various components of the invention can of course be made. The invention resides as well in sub-combinations and sub-systems of the elements described, and in methods of using them.

DETAILED DESCRIPTION OF THE INVENTION

While the present invention has been described with references to preferred embodiments, various changes or substitutions may be made on these embodiments by those ordinarily skilled in the art pertinent to the present invention without departing from the technical scope of the present invention. Therefore, the technical scope of the present invention encompasses not only those embodiments described above, but also all that fall within the scope of the appended claims.

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges included herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

As used herein, the terms "comprises," "comprising," "includes," "including," "has," "having" or any other variation thereof, are intended to cover a non-exclusive inclusion. For example, a process, method, article or apparatus that comprises a list of elements is not necessarily limited to only those elements, but may include other elements not expressly listed or inherent to such process, method article or apparatus.

Embodiments of the present invention comprise improved methods for determining the concentration of anionic polymers and/or oligomers in industrial water samples. The methods disclosed and claimed herein are particularly well suited for quickly and accurately determining the concentration of anionic polymer corrosion or scale inhibitors in aqueous systems, including but not limited to boilers, cooling towers, evaporators, gas scrubbers, kilns and desalination units. The method includes the use of predetermined calibration curves for optimal efficiency and effectiveness. Polymers capable of being detected by the methods disclosed herein include, but are not limited to, water-soluble anionic polymers that contain anionic groups, such as carboxylate, sulfonate, sulfate, phosphonate, phosphate. Examples of the same are polyacrylic acid moiety polymers, polysufonated polymers, and maleic anhydride polymers. Some specific examples of contemplated anionic polymers are HPS-1, AEC and APES (GE Betz, Trevose, Pa.).

Figure 1:
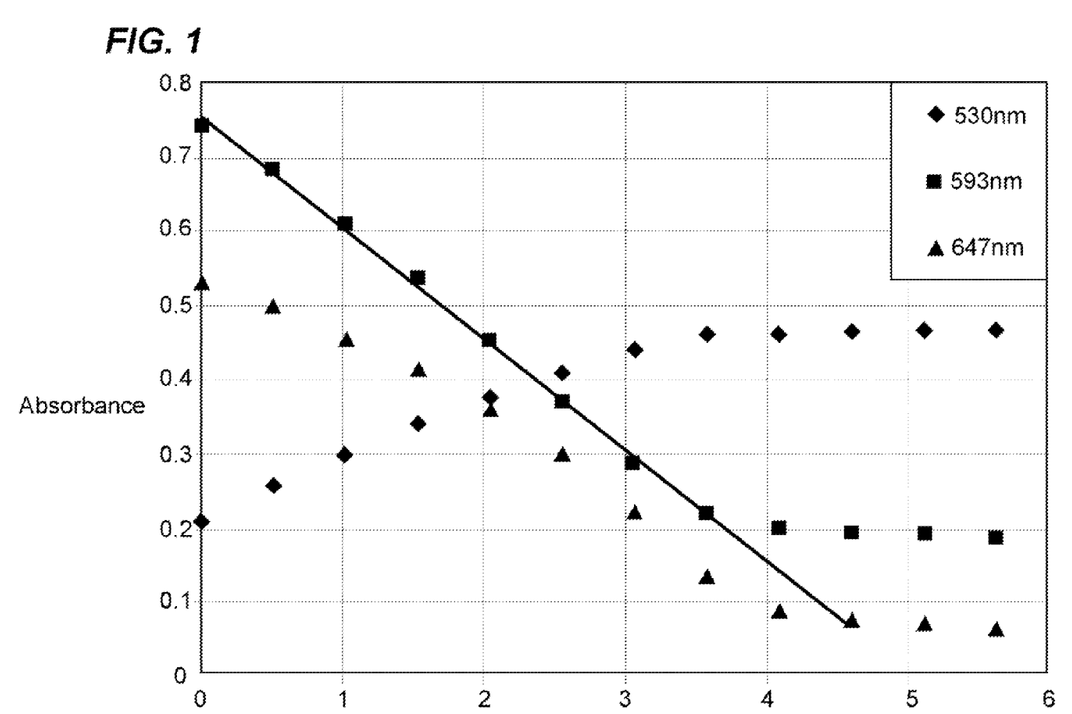
FIG. 1 depicts the plot of absorbance change of 1,9-dimethyl methylene blue at 530, 593 and 647 nm as a function of the concentration of polymer HPS-I.
Figure 2:
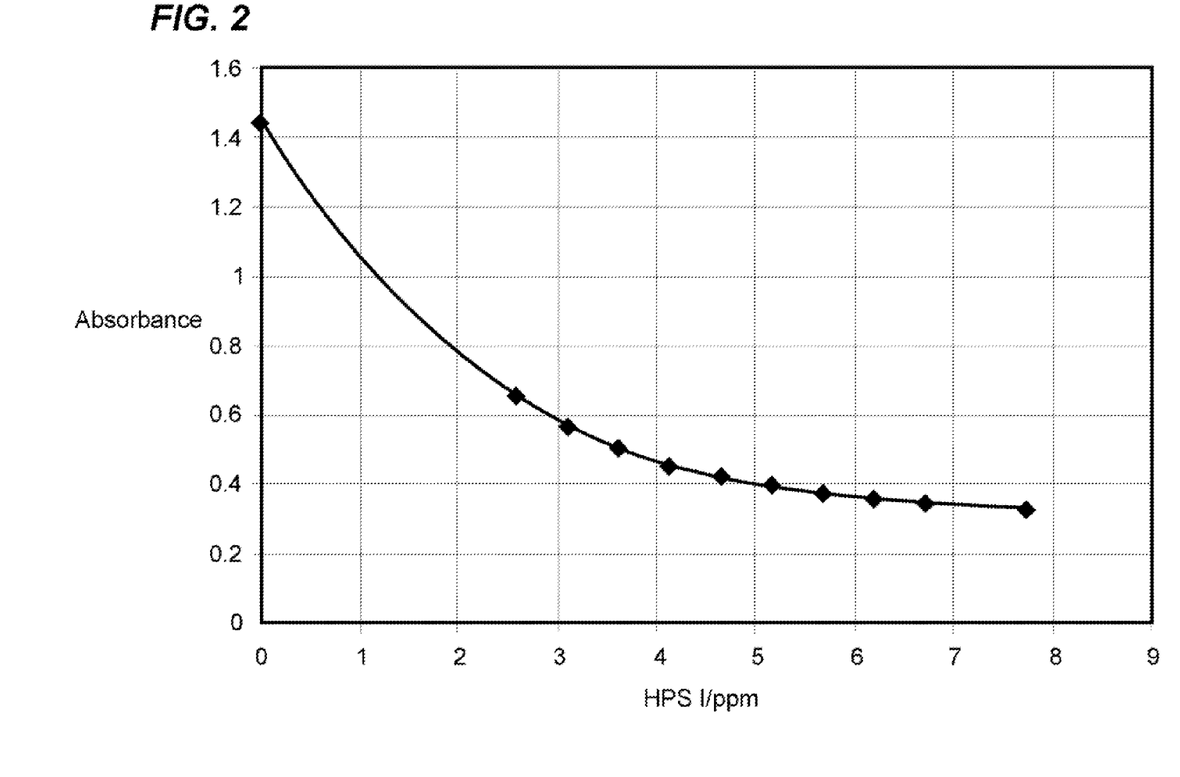
FIG. 2 depicts the plot of absorbance change of Azure B at 593 nm as a function of the concentration of polymer HPS-I.

One factor that needs to be evaluated for each particular polymer is its degree of interaction between that polymer and a dye. This factor can be determined by mapping the absorbance change of a dye as a function of a particular polymer. In order to determine the change in absorbance of a dye composition, an initial absorbance of the dye composition is determined at a set time after mixing the composition at any wavelength in the visible spectrum of 300 to 700 nm. In the present application, these measurements were repeated as a function of a particular polymer concentration. FIG. 1, as an example, shows the absorbance change of 1,9-dimethyl methylene blue (DMMB) at 530, 593 and 647 nm, as a function of polymer HPS-I (acrylic acid/1-allyoxy, 2-hydroxypropylsulfonate), and its concentration. FIG. 2 shows the absorbance change of an alternate dye, Azure B (AB) as a function of HPS-I at 593 nm. Therefore, it is possible to quantify the degree of interaction between a particular dye and any polymer, such as, but not limited to, HPS-I. To one skilled in the art, examination of FIG. 1 and FIG. 2 clearly indicates that the exhibited interaction between DMMB and HPS-I is much stronger than the interaction between AB and HPS-I.

Figure 3:
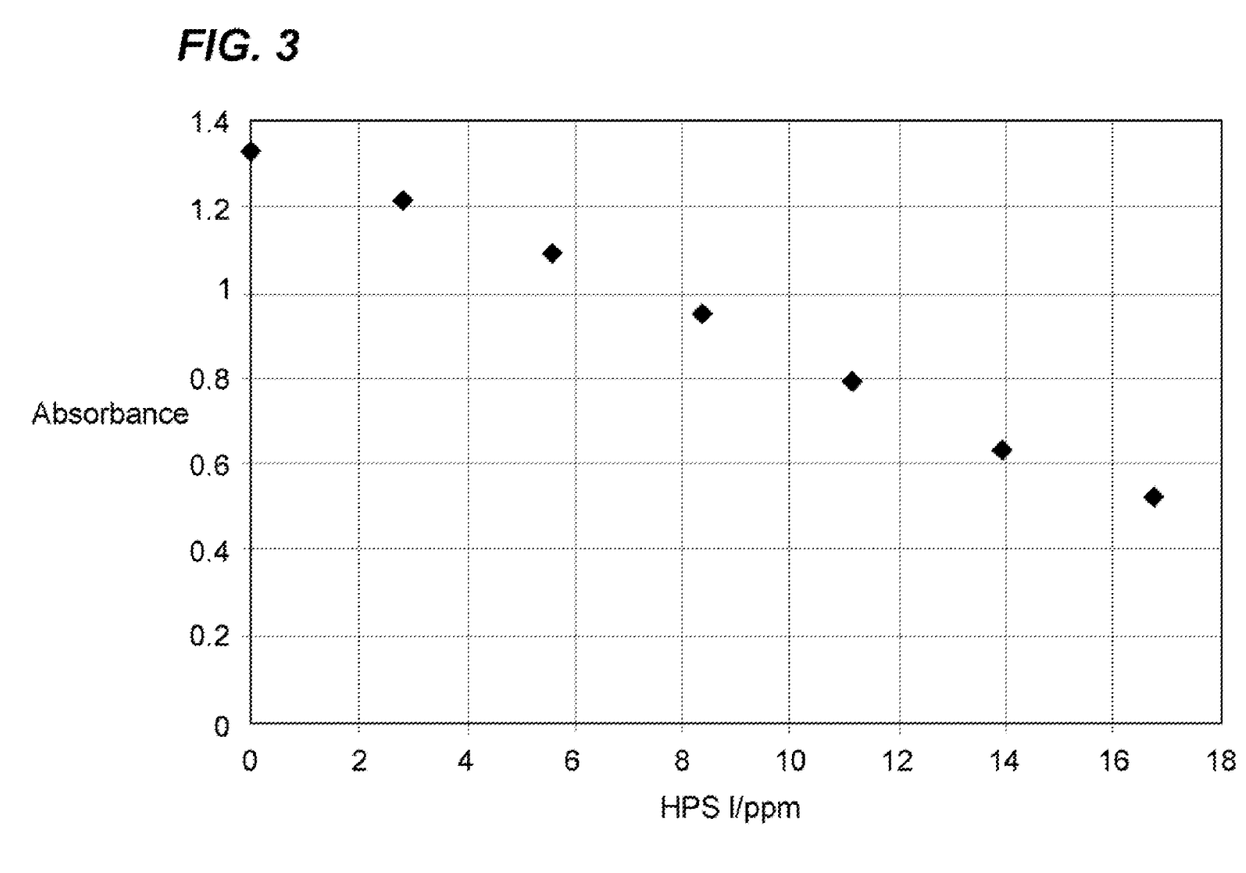
FIG. 3 depicts the plot of the absorbance change of Brilliant Crystal Blue as a function of the concentration of polymer HPS-I.

Another factor that is considered in an embodiment of the present invention is the ionic strength effect. FIG. 3 shows the absorbance of brilliant crystal blue (BCB) dye at 585 nm as a function of concentration of HPS-I polymer. BCB exhibits even weaker interaction toward HPS-I than AB, when comparing the plots in FIGS. 3 and 2. This is relevant in that the weaker the interaction, the less desirable the dye and polymer combination.

Figure 4:
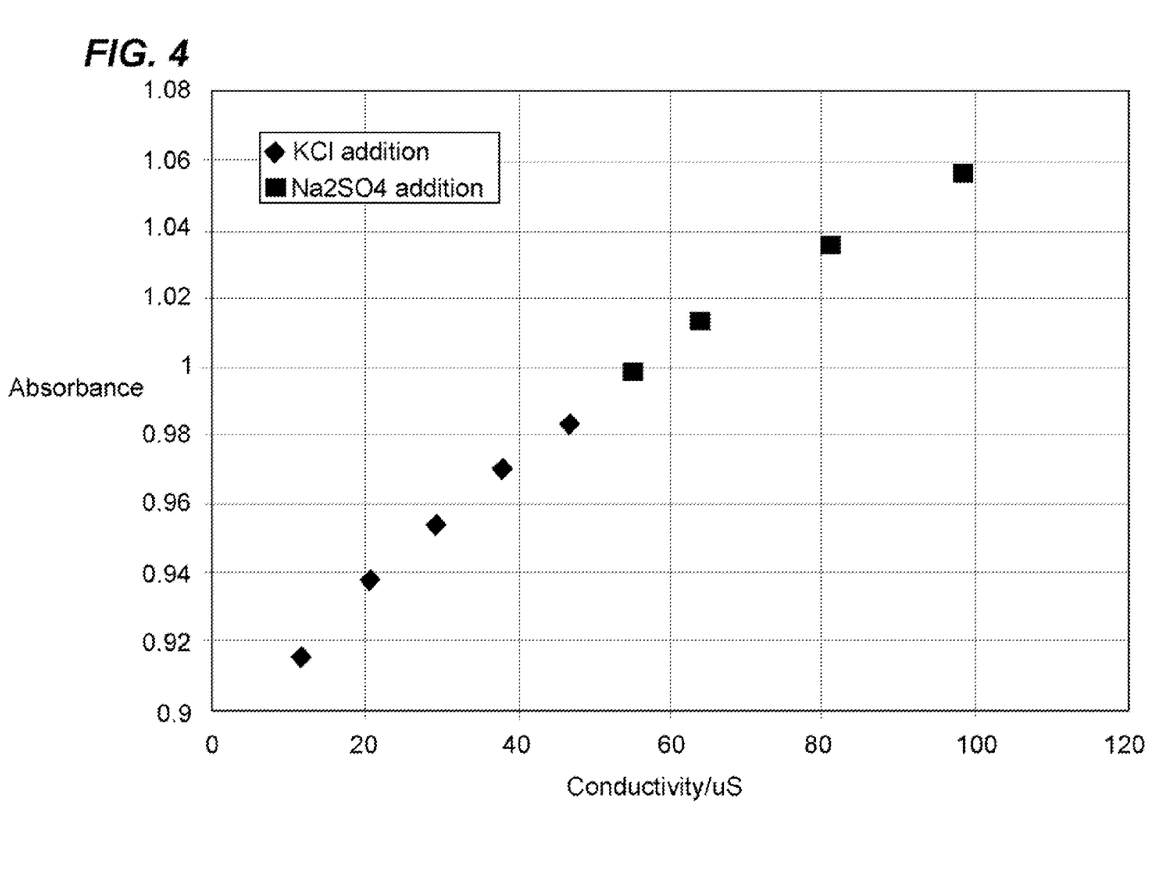
FIG. 4 depicts the plot of the absorbance change of Brilliant Crystal Blue (BCB) at 585 nm for a 2 ppm concentration of polymer HPS-I as a function of solution conductivity.

FIG. 4 depicts another factor that can be considered in an embodiment of the present invention. Specifically, FIG. 4 shows absorbance change of BCB at 585 nm for a 2 ppm HPS-I polymer concentration, as a function of solution conductivity. The value of conductivity is a quantitative indication of ionic strength. The ionic strength effect is pronounced for BCB, and therefore suggests that BCB is not a good dye for HPS-I determination in real water samples, since it is too difficult to control the ionic strength of the sample. The information gleamed from FIG. 4, in conjunction with the information determined from FIGS. 1 and 2, demonstrates that for the proper dyes needs to be selected in order to have the most accurate readings of polymers or oligomers present in an aqueous solution. Specifically, a dye needs to be used that has a strong interaction with the polymer in question, in order to minimize possible interference from the water matrix. At present, processes that take into account the combined effect of factors such as polymer/dye interaction, ionic strength, and solution conductivity have not been known to date. The data generated from studying these interactions lead to the presently claimed process.

Cationic and anionic dyes and polymers are water-soluble due to the fact that they possess charges; i.e. they are positively or negatively charged. When a dye forms a complex with a polymer, the total ionic charge carried by the complex is reduced due to mutual charge neutralization. An example would be the interaction of a negative dye and a positively charged polymer. As a result of this interaction, the dye-polymer complex may precipitate from the assay system. Such an action can become problematic, particularly in situations where the aqueous system is one with a high hardness factor. Multifunctional buffers may be added in an embodiment of the present invention, to address some of the factors that limit the ability to quickly and accurately measure the presence of polymers and/or oligomers in aqueous solutions. Multifunctional buffers are compositions or solutions that include, but are not limited to, stabilizing agents, masking agents, and/or pH buffers, and combinations thereof. Such multifunctional buffers have not been known nor used in the prior art, and provide a great service relative to the issue of interference in correct determination of polymer/oligomer concentration in solutions. The use of such a multifunctional buffer addresses the issues of selectivity and stability by minimizing or eliminating the factors that effect effective and efficient determination of polymer concentration, and make the present method practical for use in current industrial facilities.

Figure 5:
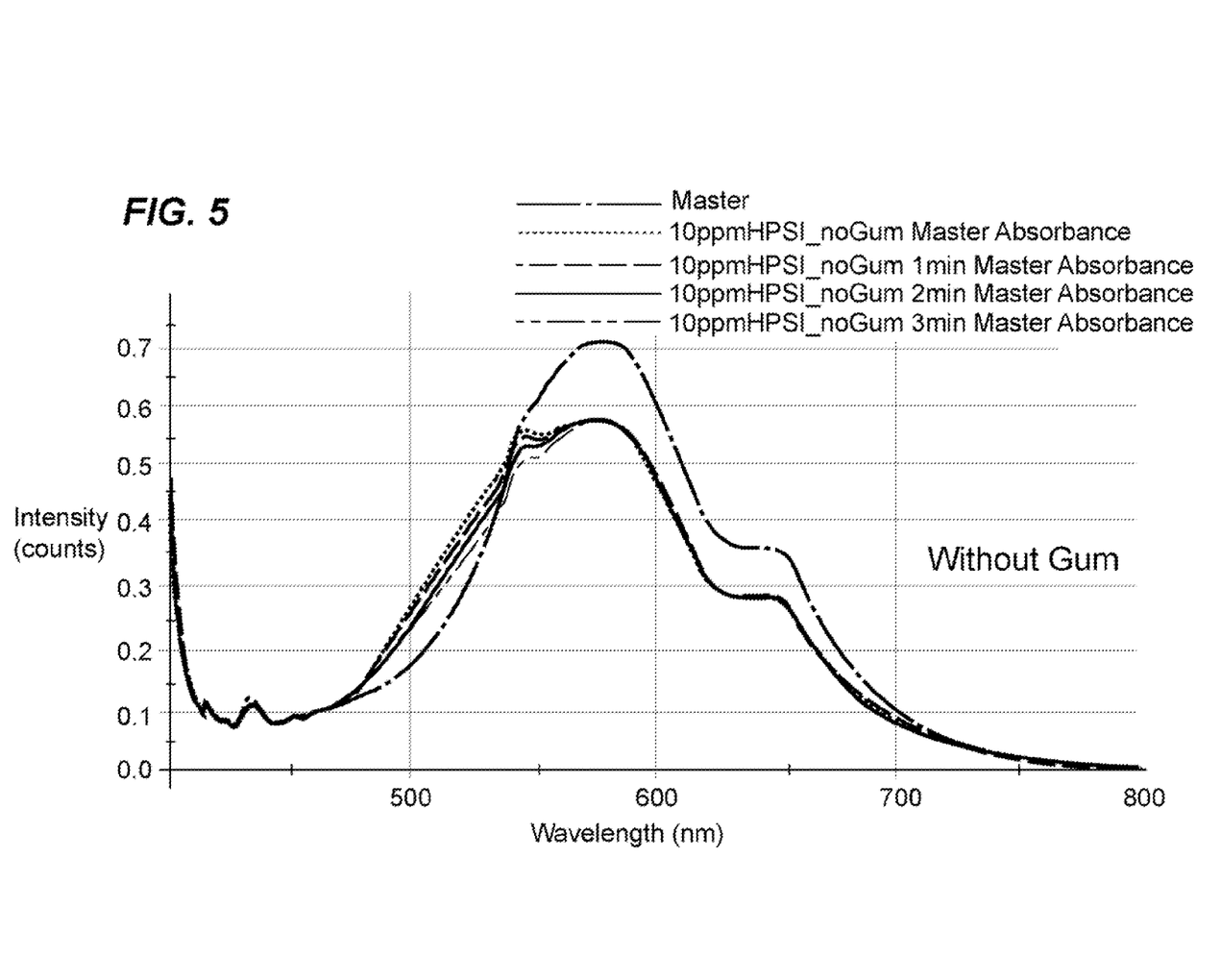
FIG. 5 is a depiction of the precipitation of DMMB dye upon the addition of HPS-I.
Figure 6:
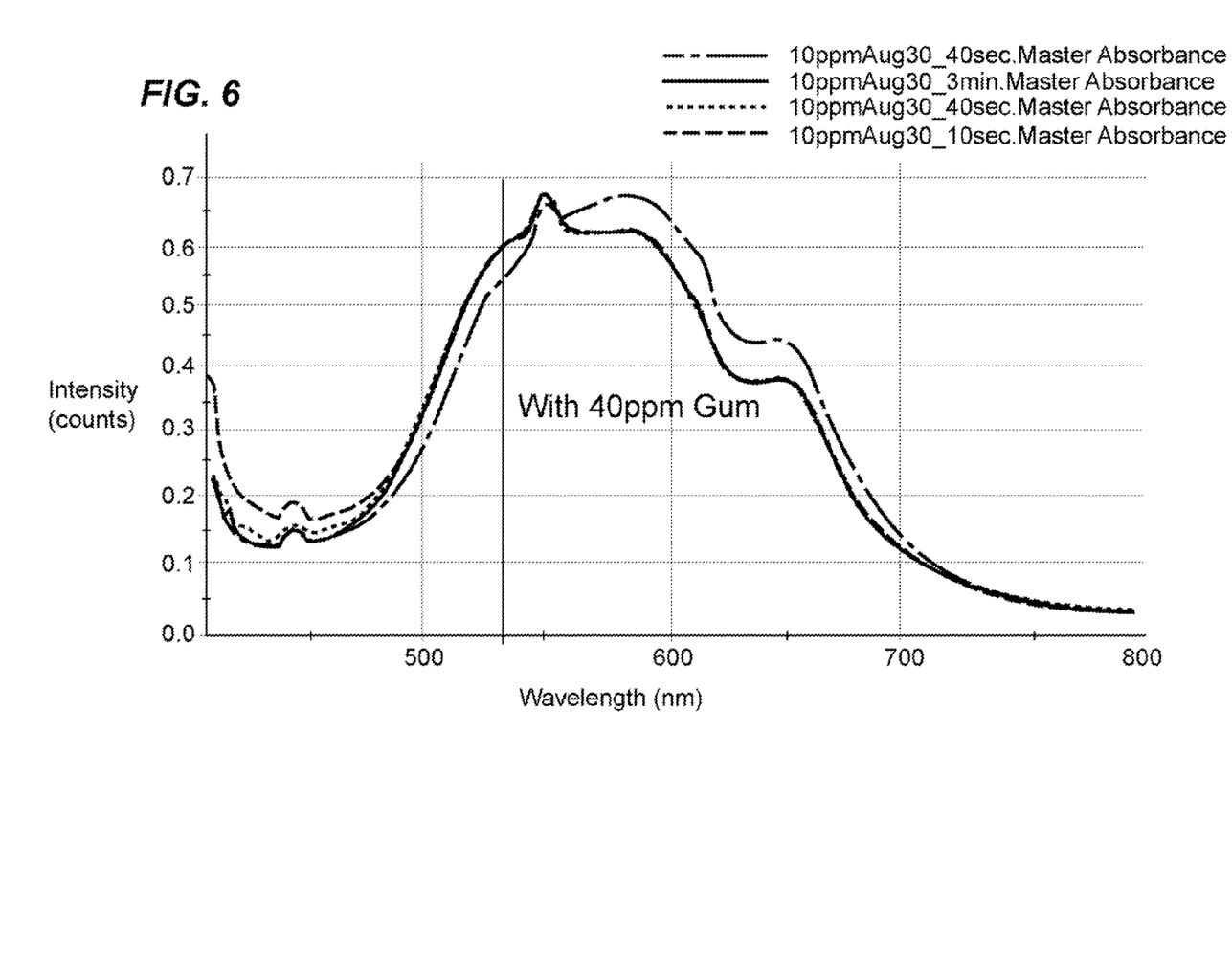
FIG. 6 is a depiction of the same assay of FIG. 5, but with the addition of 40 ppm Arabic gum.

An embodiment of the invention includes the addition of a stabilizing agent in order to more accurately determine polymer/oligomer concentration in an aqueous solution. Addition of a stabilizer agent assists with solving the issue of precipitation and assay instability. FIG. 5 shows that DMMB precipitates quickly from the assay solution upon addition of a polymer, in this instance HPS-I. FIG. 6 shows the same assay and polymer interaction, but with the addition of a stabilizing agent, which shows decreased precipitation. In particular, FIG. 6 shows that DMMB does not precipitate nearly as much or as quickly after the addition of the polymer HPS-1, due to the presence of a stabilizing agent, in this case, Arabic gum. A stable assay free of precipitation is required for online or automatic application where precipitation could result in blockage of a flow and deposition on an optical window, for example. A stabilizer may be added in varying amounts, such as from about 10 to about 100 ppm, or about 30 to about 50 ppm.

Figure 7:
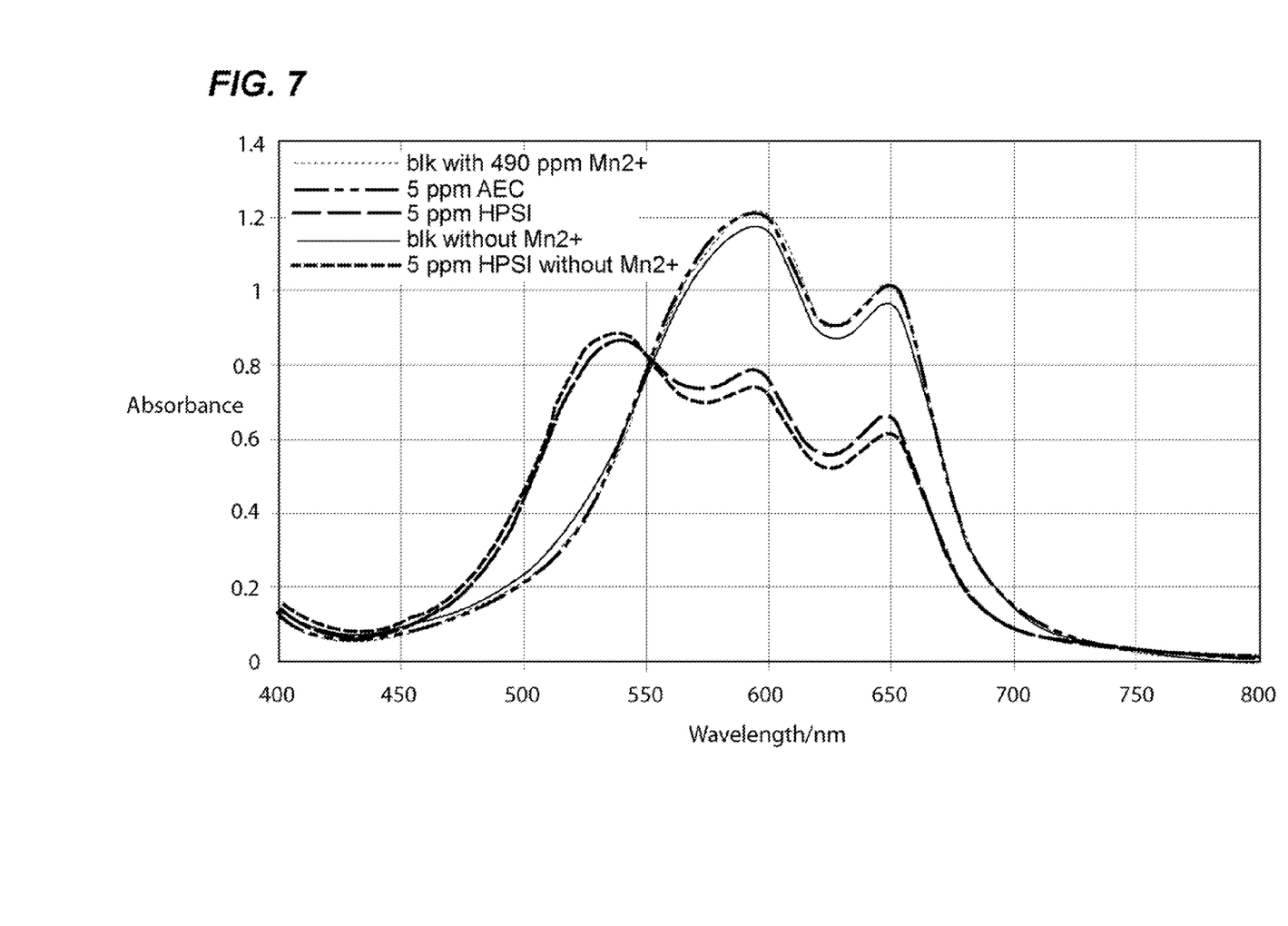
FIG. 7 depicts the use of $Mn^{2+}$ as a masking agent for AEC.

Another embodiment of the invention provides for the masking of surfactants that may be present with the polymers and/or oligomers. An anionic surfactant can be effectively masked by including a masking agent in the multifunctional buffer. By including such a masking agent, the reading of the polymer concentration is more accurate. FIG. 7 demonstrates that 5 ppm of poly epoxysuccininc acid (PESA) does not exhibit any response to the dye in the presence of 490 ppm Mn in the buffer. Dodecylbenzene sulfonate is an example of another anionic surfactant that can be masked by adding a cationic surfactant to the aqueous system. The masking agent in an amount of from 20 ppm to about 2000 ppm, and further from about 100 ppm to about 1000 ppm. Masking agents include, but are not limited to, bivalent manganese salt, ferrous salt, calcium salts, zinc salts, quaternary amine surfactant, or combinations thereof.

Certain components naturally exist in water and aqueous systems. For example, tannic acid is one of the naturally occurring components that exist in surface water. Tannic acid is likely to cause severe interference to metachoromatic dye-based calorimetric methods when determining the concentration of anionic polymers, such as synthetic anionic polymers. It has been found that the polymers HPS-I and PESA do not respond to cationic dye, such as, but not limited to, Basic Blue 17 while in the presence of water with a high hardness concentration. However, tannic acid exhibits a sensitive response to a dye, such as Basic Blue 17 (BB 17), in the presence of an aqueous system with a high hardness concentration. Therefore, an alternate embodiment of the present invention calls for a two-dye method for determining both anionic polymeric concentration, such as HPS-I, and tannic acid concentration. This can be accomplished by first measuring a total response of an aqueous system to a cationic dye, such as DMMB, wherein the aqueous system comprises both tannic acid and an anionic polymer, such as HPS-I. Thereafter, a second cationic dye, such as BB 17, is exposed to the aqueous system, and the absorbance response from that exposure is measured. Since the second dye, in this case BB 17, does not respond to the anionic polymer, in this case HPS-I, then the absorbance measured with this second dye is clearly related to other components, such as tannic acid. Therefore the simple subtraction of the concentration of the second component or group of components measured by the second dye, from the initial reading of the overall response, will result in the measurement of the anionic polymer in the system, i.e. in this case the concentration of HPS-I.

In one embodiment of the invention, the method for determining the concentration of an anionic polymer or oligomer in an industrial water sample comprises adding a multifunctional buffer solution to the industrial water sample, subsequently adding a cationic dye solution to the water sample comprising the buffer resulting in an admixture, measuring the absorbance of the admixture at a selected wavelength, and determining the polymer or oligomer concentration from the absorbance value based on a predetermined calibration equation. The calibration for a particular polymer is determined by plotting the absorbance at a set wavelength as a function of the concentration of a polymer.

The portion or sample of the industrial water sample may be any convenient amount of the aqueous solution containing the polymer or oligomer compounds. Additionally, pretreatment of the water sample may be desirable, such as filtration of the sample to remove particulates, addition of an effective amount of a reducing agent to reduce chlorine and/or ferric iron, if present, thereby minimizing interference from these components.

The dyes are chosen from a group of metachromatic dyes, which are dyes that undergo a color change upon interaction with polyionic compounds. The group of dyes from which the cationic dyes are chosen includes, but is not limited to, Dimethyl Methylene Blue, Basic Blue 17, New Methylene Blue, and combinations thereof. One embodiment of the invention calls for the use of 1,9-dimethyl methylene blue as the cationic dye. The cationic dye is added in an effective amount, which amount is generally from about 0.5 to about 3.0 times the molar concentration of the polymer in the assay.

An alternate embodiment of the invention calls for the use of a second or additional multifunctional buffer. In that embodiment, the method for determining the concentration of an anionic polymer or oligomer in an industrial water sample by means of differential masking, comprises adding a first multifunctional buffer solution to a portion of said sample, followed by adding a cationic dye solution to the sample-buffer mixture to create an admixture; measuring the absorbance of the admixture at a selected wavelength(s), followed by adding a second multifunctional buffer to the a second portion of the industrial water sample to create a second buffer-water mixture, adding the cationic dye solution to the second buffer-water mixture, measuring absorbance of the admixture resulting from the second mixture, and determining the polymer and oligomer concentration from the two absorbance values based on a predetermined calibration equation. In one embodiment comprising the use of two multifunctional buffer solutions, the multifunctional buffers comprise at least one masking agent each, which the masking agents can be the same or different in each buffer solution, as well as present in the same or different amounts in the buffer solution, and any combination thereof.

Another embodiment of the invention follows the steps above, but differs in that the sample is determine by means of inference background correction, using a second or alternate cationic dye which is mixed in with the second water-buffer mixture to form a second admixture. Therefore, in this instance the process comprises adding a multifunctional buffer solution to a portion of a water sample, adding a first cationic dye solution to the initial sample-buffer mixture, determining absorbance of the initial admixture at a selected wavelength or wavelengths and then repeating these steps wherein the first cationic dye solution is replaced by a second cationic dye solution. Thereafter the polymer and oligomer concentrations are obtained from the absorbance values perceived in the process above and using a predetermined calibration equation.

Absorbance, as used herein, may be defined according to the Lambert-Beer Law as follows:

$$A = abc$$

where A=absorbance; a=absorbtivity of the dye; b=light path length; and c=concentration of the colored substance. Each dye used will have a maximum absorbance within the 300 to 1000 nm range, and it is desirable to measure absorbance at a wavelength within the range of maximum absorbance.

Absorbance may be measured using any suitable device known in the art to measure absorbance. Such suitable devices include, but are not limited to, calorimeters, spectrophotometers, color-wheels, and other types of known color-comparative measuring tools. One embodiment provides for measurements of optical response performed using an optical system that includes a white light source (such as a Tungsten lamp available from Ocean Optics, Inc of Dunedin, Fla.) and a portable spectrometer (such as Model ST2000 available from Ocean Optics, Inc. of Dunedin, Fla.). Desirably, the spectrometer used covers the spectral range from about 250 nm to about 1100 nm.

Figure 8:
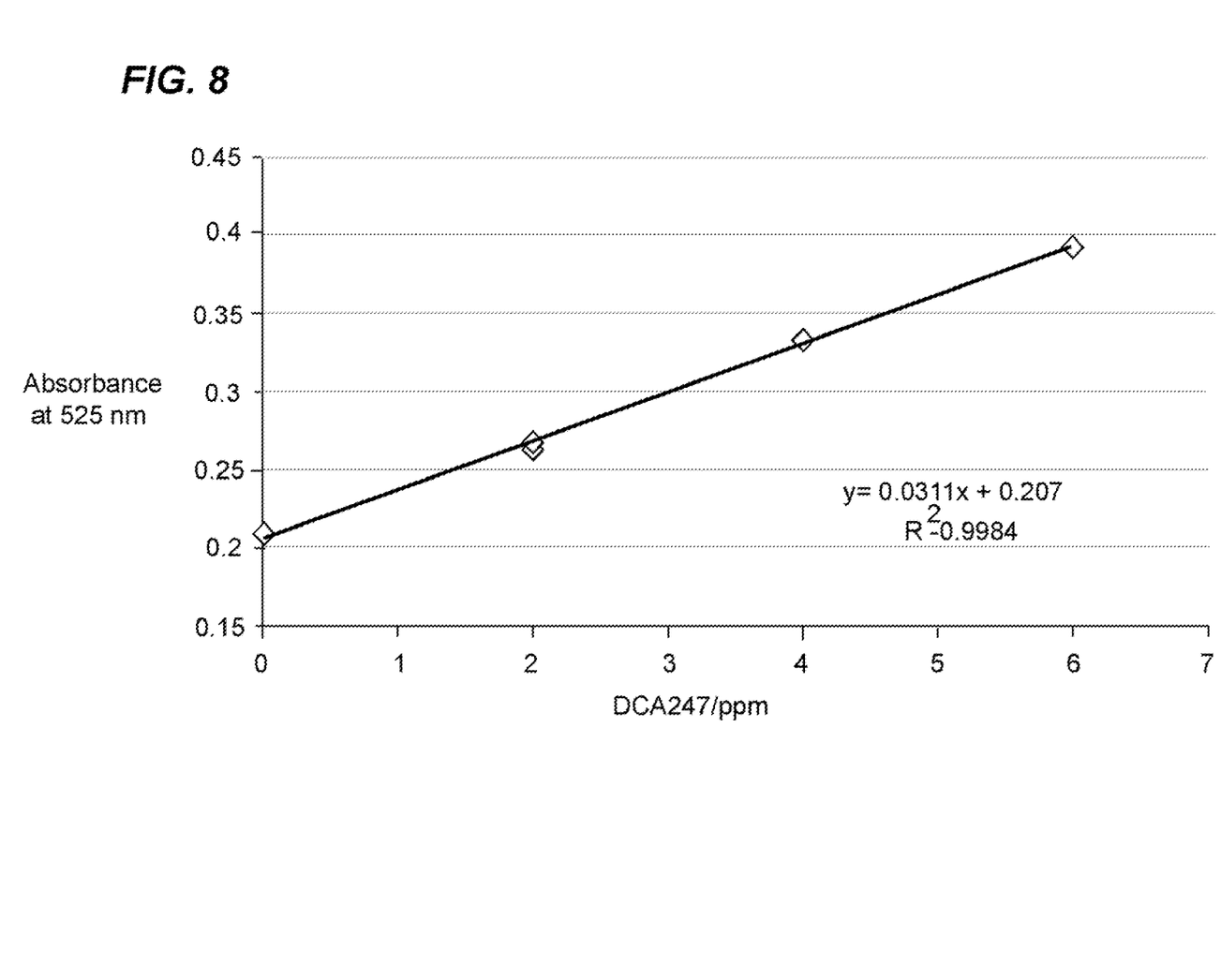
FIG. 8 depicts a calibration curve for DCA 247.

In order to determine the concentration or amount of available anionic polymer in an industrial water system, it is first necessary to generate a calibration curve for each polymer of interest. Calibration curves are generated by preparing various samples of water containing known amounts of polymer, making an appropriate reagent solution and measuring the absorbance of the sample suing the reagent solution. In one embodiment of this invention, absorbance is being reported as absorbance difference. Absorbance difference is the difference between the absorbance of the reagent solution by itself and the absorbance of the mixture of reagent solution and the sample of water being tested. The calibration curve is then a plot of this absorbance difference vs. the known concentration of the polymer in the sample. Once created the calibration curve can be used to tell how much polymer is present in a sample by comparing the measured absorbance difference of the sample with the curve and reading the amount of polymer present off of the curve. An example of such a curve is set forth in FIG. 8, which depicts a calibration curve for DCA 247.

It should be understood that various changes and modifications to the present embodiments as described herein will be apparent to those skilled in the art. Such changes and modifications can be made without departing from the spirit and scope of the present invention and without diminishing its attendant advantages. It is therefore intended that such changes and modifications be covered by the appended claims.

The invention is illustrated in the following non-limiting examples, which are provided for the purpose of representation, and are not to be construed as limiting the scope of the invention. All parts and percentages in the examples are by weight unless indicated otherwise.

EXAMPLE

A calibration curve was determined for DCA 247 (GE Betz, Trevose, Pa.). A 1,9-dimethyl methylene blue (DMMB) solution was prepared comprising 100 ppm DMMB in deionized water. The buffer pH was 4.2, and was prepared from 0.1M acetic acid and 1M sodium hydroxide in deionized water. The buffer solution contained 100 ppm Arabic gum as a stabilizing agent and 5000 ppm manganese sulfate monohydrated as a masking agent to eliminate poly epoxysuccininc acid (PESA) interference. The absorbance was measured at 525 nm and plotted as a function of the concentration of DCA 247. The calibration equation was y=0.0311x+0.207 and $R^2$=0.9984. The results are set forth in FIG. 12.

What is claimed is:

1. A method for determining the concentration of an anionic polymer or oligomer in an industrial water sample comprising:
   (a) adding a multifunctional buffer solution to said sample, wherein said multifunctional buffer solution comprises at least one masking agent selected from the group consisting of bivalent manganese salt, ferrous salt, calcium salt, zinc salt and combinations thereof;
   (b) adding a cationic dye solution to the buffer-sample mixture of step (a);
   (c) measuring absorbance of the admixture in step (b) above at a selected wavelength or wavelengths; and
   (d) determining polymer or oligomer concentration from the absorbance values determined in step (c) based on a predetermined calibration equation.

2. The method of claim 1 wherein said multifunctional buffer of step (a) further comprises a stabilizing agent capable of decreasing precipitation of the cationic dye in said admixture.

3. The method of claim 1 wherein the multifunctional buffer of step (a) additionally comprises a pH buffer.

4. The method of claim 1 wherein the cationic dye is chosen from the group consisting of Dimethyl Methylene Blue, Basic Blue 17 and New Methylene Blue N, and combinations thereof.

5. The method of claim 1 wherein the cationic dye is chosen from the group consisting of 1,9-dimethyl methylene blue.

6. The method of claim 2 wherein the stabilizing agent is Arabic gum.

7. A method for determining the concentration of an anionic polymer or oligomer in an industrial water sample by means of differential masking comprising:
   (a) adding a first multifunctional buffer solution to a portion of said sample:
   (b) adding a cationic dye solution to the sample-buffer mixture of step (a);
   (c) measuring absorbance of the admixture in step (b) at a selected wavelength or wavelengths;
   (d) adding a second multifunctional buffer to a second portion of said sample;
   (e) adding said cationic dye solution to the sample-buffer mixture from step (d);
   (f) measuring absorbance of the admixture resulting from step (e);
   (g) determining polymer and oligomer concentration from the absorbance values obtained from both steps (c) and (f) based on a predetermined calibration equation;
   wherein said first multifunctional buffer solution and said second multifunctional buffer each comprises at least one masking agent selected from the group consisting of bivalent manganese salt, ferrous salt, calcium salt, zinc salt and combinations thereof.

8. The method of claim 7 wherein said first multifunctional buffer of step (a) further comprises a stabilizing agent capable of decreasing precipitation of the cationic dye in said admixture of step (b).

9. The method of claim 7 wherein said second multifunctional buffer of step (d) further comprises a stabilizing agent capable of decreasing precipitation of the cationic dye in said admixture of step (e).

10. The method of claim 7 wherein said first multifunctional buffer is comprised of at least one masking agent different from the masking agent of the second multifunctional buffer.

11. The method of claim 7 wherein said first multifunctional buffer comprises a masking agent which is present in a non-equal amount to the masking agent present in the second multifunctional buffer.

12. The method of claim 7 wherein said first multifunctional buffer additionally contains a pH buffer.

13. The method of claim 7 wherein said second multifunctional buffer additionally contains a pH buffer.

14. The method of claim 7 wherein the cationic dye is chosen from the group consisting of Dimethyl Methylene Blue, Basic Blue 17 and New Methylene Blue N, and any combination thereof.

15. The method of claim 7 wherein the cationic dye is 1,9-dimethyl methylene blue.

16. The method of claim 8 wherein the stabilizing agent is arabic gum.

17. The method of claim 9 wherein the stabilizing agent is arabic gum.

18. A method for determining the concentration of an anionic polymer or oligomer in an industrial water sample by means of interference background correction using a second dye solution comprising:
- (a) adding a multifunctional buffer solution to a portion of said sample, wherein said multifunctional buffer solution comprises at least one masking agent selected from the group consisting of bivalent manganese salt, ferrous salt, calcium salt, zinc salt and combinations thereof;
- (b) adding a first cationic dye solution to the sample-buffer mixture of (a);
- (c) determining absorbance of the admixture resulting from step (b) at a selected wavelength or wavelengths;
- (d) repeating steps (a), (b) and (c) wherein said first dye solution is replaced by a second dye solution;
- (e) obtaining polymer and oligomer concentration from the absorbance values obtained from steps (c) and (d) and using a predetermined calibration equation.

19. The method of claim 18 wherein the first cationic dye is chosen from the group consisting of Dimethyl Methylene Blue, Basic Blue 17 and New Methylene Blue N, and any combination thereof.

20. The method of claim 18 wherein the second cationic dye is chosen from the group consisting of Dimethyl Methylene Blue, Basic Blue 17 and New Methylene Blue N, and any combination thereof.

21. The method of claim 18 wherein the first cationic dye and the second cationic dye are chosen from the group consisting of Dimethyl Methylene Blue, Basic Blue 17 and New Methylene Blue N, and combinations thereof, but the first cationic dye is not the same as the second cationic dye.

22. The method of claim 18 wherein said multifunctional buffer of step (a) additionally comprises stabilizing agent capable of decreasing precipitation of the cationic dye in said admixture.

* * * * *

UNITED STATES PATENT AND TRADEMARK OFFICE
CERTIFICATE OF CORRECTION

PATENT NO. : 8,178,353 B2
APPLICATION NO. : 11/755935
DATED : May 15, 2012
INVENTOR(S) : Xiao et al.

It is certified that error appears in the above-identified patent and that said Letters Patent is hereby corrected as shown below:

In Column 5, Line 17, delete "Mn" and insert -- $Mn^{+2}$ --, therefor.

In Column 5, Line 29, delete "calorimetric" and insert -- colorimetric --, therefor.

In Column 7, Line 1, delete "calorimeters," and insert -- colorimeters, --, therefor.

Signed and Sealed this
Twentieth Day of November, 2012

David J. Kappos
*Director of the United States Patent and Trademark Office*